May 20, 1952 G. MERRILL Plant Pat. 1,098

PEACH TREE

Filed Oct. 27, 1950

WITNESS

Addison E. Avery

INVENTOR

Grant Merrill

Webster & Webster

ATTYS.

Patented May 20, 1952

Plant Pat. 1,098

UNITED STATES PATENT OFFICE 1,098

PEACH TREE

Grant Merrill, Red Bluff, Calif.

Application October 27, 1950, Serial No. 192,552

1 Claim. (Cl. 47—62)

This invention pertains to a new and distinct variety of peach tree which bears yellow-fleshed freestone fruit; the prime features of distinction being that the fruit resembles the Rio Oso Gem (U. S. Plant Patent No. 84), but ripens slightly later than the Kirkman Gem (U. S. Plant Patent No. 506).

The parent tree of the herein claimed variety is a seedling of the Kirkman Gem; seeds of the latter variety having been planted by me in February 1946 in my experimental plot on my farm near Red Bluff, California. The parent tree first fruited and was observed in September 1948; it having been recognized at that time that the variety was favorably distinguished from both the Rio and Oso Gem and the Kirkman Gem in the respects which will be hereinafter noted.

Subsequent to discovery of the new variety, and observation of the fruit borne thereon, such new variety has been successfully asexually reproduced by cleft grafting onto mature Golden Jubilee trees in my orchard near Red Bluff, California; the reproductions now bearing and carrying forward all of the novel characteristics of the parent tree and its fruit.

The fruit of the present variety generally resembles that of the Rio Oso Gem, but is an improvement, or is otherwise advantageous marketwise, by reason of a ripening period which is approximately five weeks later; is sweeter; smoother skinned; more symmetrical in form; and with less ridge down the suture line.

As compared to the Kirkman Gem, the fruit of the instant variety ripens a few days later; is much sweeter; is firmer; and does not have the soft suture stripe which characterizes said Kirkman Gem.

Further, the fruit of the claimed variety does not darken on exposure of the flesh to air.

Figure 1:
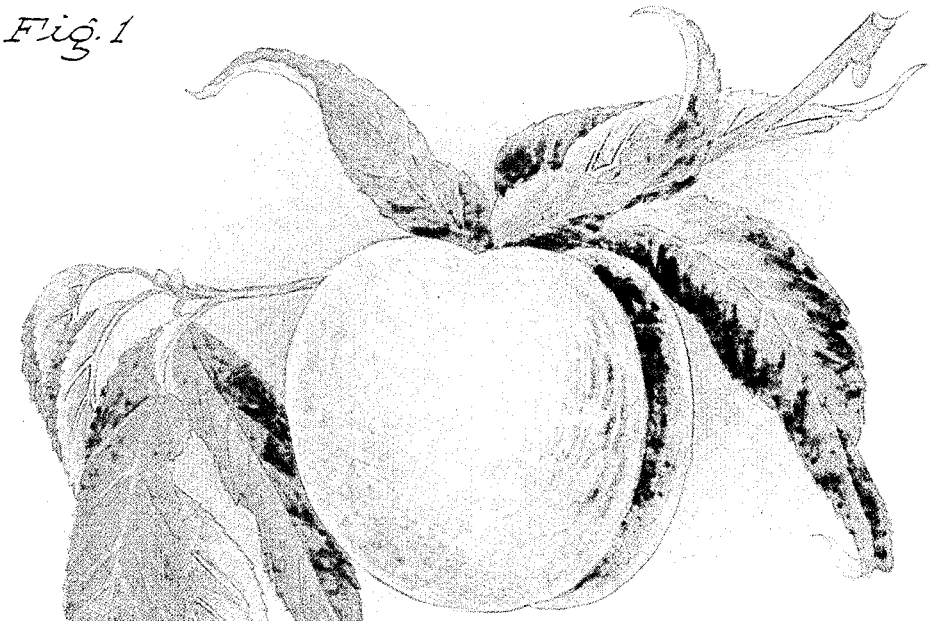
Fig. 1 is a perspective view of a fruit of the variety in connection with a stem and leaves.
Figure 2:
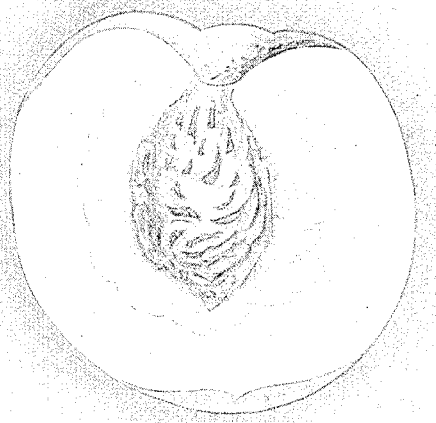
Fig. 2 is a sectional view taken axially of one of the fruit, with the stone exposed.

Referring now more specifically to the pomological details of the new and distinct variety of peach tree, the following is an outline description thereof; all major color plate identifications being by reference to Maerz and Paul Dictionary of Color.

Tree: Medium size; medium vigorous; medium upright; vase formed; productive; regular bearer.

Trunk: Medium stocky; medium shaggy.

Branches: Medium stocky; medium shaggy; reddish brown; somewhat glossy. *Lenticels*—numerous.

Leaves: Average length—6″; average width 1¼″. Acuminate — lanceolate; acutely pointed; thin; smooth to slightly rugose along midriff. Color—medium green (23–L–2) on top side; lighter yellowish green (22–J–5) on under side.

*Stem twigs.*—Medium brown (8–L–11).

*Margin.*—Base glandular; crenate, except tip serrate.

*Petiole.*—Medium length; medium thick.

*Glands.*—Average none to seven, mostly five; none to three on petiole; two to six on leaf. Alternate; large; reniform. Brown to green on new growth.

Flower buds: Medium size; medium length; obtuse; free; pubescent.

Flowers: First bloom—March 5, 1950; full bloom—March 16, 1950. Early blooming; large size; pink.

Fruit: Maturity when described—firm, ripe. Date first and last picking—September 15, 1950, and September 27, 1950, respectively. Size—variable but average large. Average diameter axially — 3″; average transverse in suture plane—3″; average cheek to cheek—3″.

*Form.*—Fairly uniform; fairly symmetrical; globose.

*Suture.*—Shallow; extends from beyond apex ⅔ distance to base.

*Ventral surface.* — Lipped slightly, more prominent towards apex, but throughout and on either side.

*Cavity.*—Flaring to round. Elongated in suture plane, with suture showing on both sides. Average depth — ⅝″; average breadth—$1\frac{7}{16}$″. Marking—yellow with red blush where exposed to sunlight.

*Base.*—Truncate to retuse.

*Apex.*—Very short; retuse; very slightly depressed.

*Pistil point.*—Apical.

Skin: Thin; medium tender; tenacious to flesh; no tendency to crack.

*Color.*—Bright yellow (9–J–6) under-color, with slight red blush over entire surface, shading to red dappled to solid red (5–L–8) over half of surface.

*Down.*—Scant; very short; rolls only slightly when rubbed.

Flesh:

*Color.* — Yellow (9–L–6) streaked with red (4–L–7) next to stone and half the distance to the skin.

*Amygdaling.*—Wanting.

*Surface of pit cavity.*—Red, overlaid with cream colors.

*Fibers.*—Pink with cream color near base.

*Juice.*—Moderate; rich.

*Texture.*—Firm; meaty; abundant.

*Flavor.*—Mildly acid and sweet.

*Fibers.*—Abundant.

*Aroma.*—Slight.

*Eating quality.*—Excellent, where preference is to low acid and sweetness.

Stone: Free. Parts from flesh smoothly, retaining a small amount of flesh along ridges near base.

*Size.*—Medium. Average length—1½″; average breadth—1″; average thickness—⅝″.

*Fibers.*—Short, a few on sides.

*Form.*—Obovate; tip acuminate.

*Base.*—Oblique.

*Hilum.*—Oval.

*Apex.*—Acuminate to cuspidate.

*Sides.*—Slightly unequal.

*Surface.*—Regularly furrowed throughout, ridged from base along ventral edge, pitted throughout.

*Pits.*—Circular.

*Ventral edge.*—Thick; without wings.

*Dorsal edge.*—With shallow narrow grooves toward base to above center.

*Ridges.*—On either side; interrupted.

*Color.*—Deep tan (7–E–12) stained with reddish to purple color.

*Tendency to split.*—Slight.

Use: Market; local; dessert; culinary; canning; long distance shipment; freezing.

Keeping quality: Excellent.

Shipping quality: Good.

The tree and its fruit herein described may vary in slight detail due to climatic and soil conditions under which the variety may be grown.

Having thus described my invention, I claim:

A new and distinct variety of peach tree, substantially as described and illustrated, bearing yellow fleshed freestone fruit having the general appearance of the Rio Oso Gem but ripening approximately five weeks later than said Rio Oso Gem and a few days later than the Kirkman Gem; the fruit being sweeter than the Rio Oso Gem and Kirkman Gem; having less ridge down the suture line, being smoother skinned, and more symmetrical than the Rio Oso Gem; and being firmer, without the soft suture stripe of the Kirkman Gem; the flesh of the fruit being resistant to oxidation discoloring upon exposure of the flesh to air.

GRANT MERRILL.

REFERENCES CITED

The following references are of record in the file of this patent:

UNITED STATES PATENTS

| Number | Name | Date |
|---|---|---|
| Pl. Pt. 920 | Kirkman | Feb. 7, 1950 |